US010986990B2

(12) United States Patent
Klein et al.

(10) Patent No.: US 10,986,990 B2
(45) Date of Patent: Apr. 27, 2021

(54) MARKER PLACEMENT

(71) Applicant: COVIDIEN LP, Mansfield, MA (US)

(72) Inventors: Eyal Klein, Herzliya (IL); Israel Kehat, Ramat Hasharon (IL); Evgeni Kopel, Herzliya (IL); Alexander Y. Nepomniashchy, Haifa (IL); Oren P. Weingarten, Herzliya (IL)

(73) Assignee: Covidien LP, Mansfield, MA (US)

( * ) Notice: Subject to any disclaimer, the term of this patent is extended or adjusted under 35 U.S.C. 154(b) by 624 days.

(21) Appl. No.: 15/232,982

(22) Filed: Aug. 10, 2016

(65) Prior Publication Data
US 2017/0086665 A1    Mar. 30, 2017

Related U.S. Application Data

(60) Provisional application No. 62/232,170, filed on Sep. 24, 2015.

(51) Int. Cl.
*A61B 1/267*    (2006.01)
*A61B 5/06*    (2006.01)
(Continued)

(52) U.S. Cl.
CPC ............ *A61B 1/2676* (2013.01); *A61B 5/064* (2013.01); *A61B 5/065* (2013.01); *A61B 34/10* (2016.02);
(Continued)

(58) Field of Classification Search
CPC ....... A61B 1/2676; A61B 34/10; A61B 34/20; A61B 5/064; A61B 5/065;
(Continued)

(56) References Cited

U.S. PATENT DOCUMENTS 5,592,939 A    1/1997 Martinelli
5,611,025 A    3/1997 Lorensen et al.
(Continued)

FOREIGN PATENT DOCUMENTS

CN    101170961 A    4/2008
CN    204636425 U    9/2015
(Continued)

OTHER PUBLICATIONS

Schroeder et al. "Coil spring fiducial markers placed safely using navigation bronchoscopy in inoperable patients allows accurate delivery of CyberKnife stereotactic radiosurgery," 2010, J Thorac Cardiovasc Surg, vol. 140, pp. 1137-1142 (Year: 2010).*
(Continued)

*Primary Examiner* — Boniface N Nganga
(74) *Attorney, Agent, or Firm* — Weber Rosselli & Cannon LLP (57) ABSTRACT

A method for placing a set of one or more markers in a luminal network in a patient's body includes using at least one hardware processor for receiving image data of the anatomy of a luminal network of a patient and a location of at least one target in the luminal network anatomy; obtaining a rule set defining one or more rules for placing the set of one or more markers in the luminal network anatomy and with respect to the at least one target; during a survey performed by a user via a navigation system in a portion of the luminal network surrounding the at least one target, acquiring, via the navigation system, sample-locations in the surveyed portion of the luminal network; and identifying a set of one or more marker locations for placing the set of one or more markers from the acquired sample-locations, which complies with the rule set.

17 Claims, 6 Drawing Sheets

(51) Int. Cl.
*A61B 34/10* (2016.01)
*A61B 34/20* (2016.01)
*A61B 17/00* (2006.01)
*A61B 90/00* (2016.01)
*A61B 34/00* (2016.01)

(52) U.S. Cl.
CPC .............. *A61B 34/20* (2016.02); *A61B 34/25* (2016.02); *A61B 2017/00809* (2013.01); *A61B 2034/107* (2016.02); *A61B 2034/2051* (2016.02); *A61B 2090/365* (2016.02); *A61B 2090/3966* (2016.02); *A61B 2090/3987* (2016.02)

(58) Field of Classification Search
CPC ....... A61B 2034/107; A61B 2034/2051; A61B 34/25; A61B 2090/365; A61B 2090/3966; A61B 2090/3987; A61B 2017/00809
USPC .......................................................... 600/426
See application file for complete search history.

(56) References Cited

U.S. PATENT DOCUMENTS

| | | | |
|---|---|---|---|
| 5,676,673 A | 10/1997 | Ferre et al. | |
| 5,697,377 A | 12/1997 | Wittkampf | |
| 5,699,799 A | 12/1997 | Xu et al. | |
| 5,715,836 A | 2/1998 | Kliegis et al. | |
| 5,729,129 A | 3/1998 | Acker | |
| 5,752,513 A | 5/1998 | Acker et al. | |
| 5,782,762 A | 7/1998 | Vining | |
| 5,881,124 A | 3/1999 | Giger et al. | |
| 5,891,030 A | 4/1999 | Johnson et al. | |
| 5,913,820 A | 6/1999 | Bladen et al. | |
| 5,920,319 A | 7/1999 | Vining et al. | |
| 5,967,980 A | 10/1999 | Ferre et al. | |
| 5,971,767 A | 10/1999 | Kaufman et al. | |
| 5,987,960 A | 11/1999 | Messner et al. | |
| 6,019,725 A | 2/2000 | Vesely et al. | |
| 6,047,080 A | 4/2000 | Chen et al. | |
| 6,083,162 A | 7/2000 | Vining | |
| 6,138,045 A | 10/2000 | Kupinski et al. | |
| 6,151,404 A | 11/2000 | Pieper | |
| 6,167,296 A | 12/2000 | Shahidi | |
| 6,181,348 B1 | 1/2001 | Geiger | |
| 6,201,387 B1 | 3/2001 | Govari | |
| 6,233,476 B1 | 5/2001 | Strommer et al. | |
| 6,246,784 B1 | 6/2001 | Summers et al. | |
| 6,266,551 B1 | 7/2001 | Osadchy et al. | |
| 6,332,089 B1 | 12/2001 | Acker et al. | |
| 6,346,940 B1 | 2/2002 | Fukunaga | |
| 6,366,800 B1 | 4/2002 | Vining et al. | |
| 6,381,485 B1* | 4/2002 | Hunter .................. | G06T 3/0068 324/244 |
| 6,387,092 B1 | 5/2002 | Burnside et al. | |
| 6,466,815 B1 | 10/2002 | Saito et al. | |
| 6,496,188 B1 | 12/2002 | Deschamps et al. | |
| 6,501,848 B1 | 12/2002 | Carroll et al. | |
| 6,501,981 B1 | 12/2002 | Schweikard et al. | |
| 6,505,065 B1 | 1/2003 | Yanof et al. | |
| 6,522,907 B1 | 2/2003 | Bladen et al. | |
| 6,526,162 B2 | 2/2003 | Asano et al. | |
| 6,535,756 B1 | 3/2003 | Simon et al. | |
| 6,578,579 B2 | 6/2003 | Burnside et al. | |
| 6,584,174 B2 | 6/2003 | Schubert et al. | |
| 6,603,868 B1 | 8/2003 | Ludwig et al. | |
| 6,611,793 B1 | 8/2003 | Burnside et al. | |
| 6,650,927 B1 | 11/2003 | Keidar | |
| 6,651,669 B1 | 11/2003 | Burnside | |
| 6,694,163 B1 | 2/2004 | Vining | |
| 6,757,557 B1 | 6/2004 | Bladen et al. | |
| 6,783,523 B2 | 8/2004 | Qin et al. | |
| 6,792,390 B1 | 9/2004 | Burnside et al. | |
| 6,829,379 B1 | 12/2004 | Knoplioch et al. | |
| 6,850,794 B2 | 2/2005 | Shahidi | |
| 6,892,090 B2 | 5/2005 | Verard et al. | |
| 6,898,263 B2 | 5/2005 | Avinash et al. | |
| 6,909,913 B2 | 6/2005 | Vining | |
| 6,920,347 B2 | 7/2005 | Simon et al. | |
| 6,925,200 B2 | 8/2005 | Wood et al. | |
| 7,006,677 B2 | 2/2006 | Manjeshwar et al. | |
| 7,072,501 B2 | 7/2006 | Wood et al. | |
| 7,085,400 B1 | 8/2006 | Holsing et al. | |
| 7,096,148 B2 | 8/2006 | Anderson et al. | |
| 7,149,564 B2 | 12/2006 | Vining et al. | |
| 7,167,180 B1 | 1/2007 | Shibolet | |
| 7,174,202 B2 | 2/2007 | Bladen et al. | |
| 7,179,220 B2 | 2/2007 | Kukuk | |
| 7,236,558 B2 | 6/2007 | Saito et al. | |
| 7,301,332 B2 | 11/2007 | Govari et al. | |
| 7,315,639 B2 | 1/2008 | Kuhnigk | |
| 7,324,104 B1 | 1/2008 | Bitter et al. | |
| 7,336,809 B2 | 2/2008 | Zeng et al. | |
| 7,397,937 B2 | 7/2008 | Schneider et al. | |
| 7,428,334 B2 | 9/2008 | Schoisswohl et al. | |
| 7,452,357 B2 | 11/2008 | Vlegele et al. | |
| 7,505,809 B2 | 3/2009 | Strommer et al. | |
| 7,517,320 B2 | 4/2009 | Wibowo et al. | |
| 7,518,619 B2 | 4/2009 | Stoval, III et al. | |
| 7,630,752 B2 | 12/2009 | Viswanathan | |
| 7,630,753 B2 | 12/2009 | Simon et al. | |
| 7,659,912 B2 | 2/2010 | Akimoto et al. | |
| 7,702,153 B2 | 4/2010 | Hong et al. | |
| 7,751,865 B2 | 7/2010 | Jascob et al. | |
| 7,756,316 B2 | 7/2010 | Odry et al. | |
| 7,788,060 B2 | 8/2010 | Schneider | |
| 7,792,565 B2 | 9/2010 | Vining | |
| 7,805,269 B2 | 9/2010 | Glossop | |
| 7,809,176 B2 | 10/2010 | Gundel | |
| 7,811,294 B2 | 10/2010 | Strommer et al. | |
| 7,822,461 B2 | 10/2010 | Geiger et al. | |
| 7,901,348 B2 | 3/2011 | Soper et al. | |
| 7,907,772 B2 | 3/2011 | Wang et al. | |
| 7,929,014 B2 | 4/2011 | Akimoto et al. | |
| 7,951,070 B2 | 5/2011 | Ozaki et al. | |
| 7,969,142 B2 | 6/2011 | Krueger et al. | |
| 7,985,187 B2 | 7/2011 | Wibowo et al. | |
| 8,009,891 B2 | 8/2011 | de Vaan | |
| 8,049,777 B2 | 11/2011 | Akimoto et al. | |
| 8,055,323 B2 | 11/2011 | Sawyer | |
| 8,102,416 B2 | 1/2012 | Ito et al. | |
| 8,126,241 B2 | 2/2012 | Zarkh et al. | |
| 8,131,344 B2 | 3/2012 | Strommer et al. | |
| 8,170,328 B2 | 5/2012 | Masumoto et al. | |
| 8,199,981 B2 | 6/2012 | Koptenko et al. | |
| 8,200,314 B2 | 6/2012 | Bladen et al. | |
| 8,202,213 B2 | 6/2012 | Ito et al. | |
| 8,208,708 B2 | 6/2012 | Homan et al. | |
| 8,219,179 B2 | 7/2012 | Ganatra et al. | |
| 8,257,346 B2 | 9/2012 | Qin et al. | |
| 8,267,927 B2 | 9/2012 | Dalal et al. | |
| 8,290,228 B2 | 10/2012 | Cohen et al. | |
| 8,298,135 B2 | 10/2012 | Ito et al. | |
| 8,391,952 B2 | 3/2013 | Anderson | |
| 8,417,009 B2 | 4/2013 | Mizuno | |
| 8,494,612 B2 | 7/2013 | Vetter et al. | |
| 8,509,877 B2 | 8/2013 | Mori et al. | |
| 8,672,836 B2 | 3/2014 | Higgins et al. | |
| 8,682,045 B2 | 3/2014 | Vining et al. | |
| 8,696,549 B2 | 4/2014 | Holsing et al. | |
| 8,698,806 B2 | 4/2014 | Kunert et al. | |
| 8,700,132 B2 | 4/2014 | Ganatra et al. | |
| 8,706,193 B2 | 4/2014 | Govari et al. | |
| 8,709,034 B2 | 4/2014 | Keast et al. | |
| 8,730,237 B2 | 5/2014 | Ruijters et al. | |
| 8,768,029 B2 | 7/2014 | Helm et al. | |
| 8,784,400 B2 | 7/2014 | Roschak | |
| 8,798,227 B2 | 8/2014 | Tsukagoshi et al. | |
| 8,798,339 B2 | 8/2014 | Mielekamp et al. | |
| 8,801,601 B2 | 8/2014 | Prisco et al. | |
| 8,819,591 B2 | 8/2014 | Wang et al. | |
| 8,862,204 B2 | 10/2014 | Sobe et al. | |

(56) References Cited

U.S. PATENT DOCUMENTS

| | | | |
|---|---|---|---|
| 2005/0027193 A1* | 2/2005 | Mitschke | A61B 6/12 600/427 |
| 2005/0182319 A1* | 8/2005 | Glossop | A61B 5/061 600/424 |
| 2008/0183073 A1* | 7/2008 | Higgins | G06T 19/003 600/425 |
| 2008/0243142 A1* | 10/2008 | Gildenberg | G16H 50/50 606/130 |
| 2009/0012390 A1 | 1/2009 | Pescatore et al. | |
| 2009/0030306 A1 | 1/2009 | Miyoshi et al. | |
| 2010/0041949 A1* | 2/2010 | Tolkowsky | A61B 1/0052 600/109 |
| 2010/0310146 A1 | 12/2010 | Higgins et al. | |
| 2010/0312094 A1 | 12/2010 | Guttman et al. | |
| 2011/0085720 A1* | 4/2011 | Averbuch | A61B 90/36 382/131 |
| 2011/0237897 A1 | 9/2011 | Gilboa | |
| 2011/0251607 A1 | 10/2011 | Kruecker et al. | |
| 2012/0004518 A1* | 1/2012 | D'Souza | A61B 5/1135 600/301 |
| 2012/0046521 A1* | 2/2012 | Hunter | A61B 1/2676 600/104 |
| 2012/0046928 A1* | 2/2012 | Gibbs | G06T 19/00 703/11 |
| 2012/0203065 A1 | 8/2012 | Higgins et al. | |
| 2012/0249546 A1 | 10/2012 | Tschirren et al. | |
| 2012/0280135 A1 | 11/2012 | Bal | |
| 2012/0287238 A1 | 11/2012 | Onishi et al. | |
| 2013/0165854 A1 | 6/2013 | Sandhu et al. | |
| 2013/0223702 A1* | 8/2013 | Holsing | A61B 5/113 382/128 |
| 2013/0346051 A1 | 12/2013 | Gibbs et al. | |
| 2014/0281961 A1* | 9/2014 | Baker | G06F 3/0484 715/705 |
| 2015/0073268 A1 | 3/2015 | Stopek et al. | |

FOREIGN PATENT DOCUMENTS

| | | | | |
|---|---|---|---|---|
| WO | 2015091580 A1 | 6/2015 | | |
| WO | WO-2015091580 A1 * | 6/2015 | | A61B 5/064 |

OTHER PUBLICATIONS

Eberhardt et al. "Lung Point—a new approach to peripheral lesions," 2010, J Thorac Oncol. vol. 5, pp. 1559-1563 (Year: 2010).*

Gibbs et al. "Automated fiducial marker planning for thoracic stereotactic body radiation therapy," 2012, Proc. of SPIE vol. 8316, Medical Imaging 2012: Image-Guided Procedures, Robotic Interventions, and Modeling, pp. 83161R-1-83161R-9 (Year: 2012).*

Trumm et al. "CT Fluoroscopy—Guided Percutaneous Fiducial Marker Placement for Cyber Knife Stereotactic Radiosurgery: Technical Results and Complications in 222 Consecutive Procedures," 2014, J. Vasc. Interv. Radiol., vol. 25, pp. 760-768 (Year: 2014).*

Nabavizadeh et al. "Electromagnetic navigational bronchoscopy-guided fiducial markers for lung stereotactic body radiation therapy analysis of safety, feasibility, and interfraction stability" 2014, J. Bronchol. Intervent. Pulmonol., vol. 21, pp. 123-130 (Year: 2014).*

Gilbert et al. "Novel bronchoscopic strategies for the diagnosis of peripheral lung lesions: Present techniques and future directions," Respirology, Jul. 2014, vol. 19, No. 5, pp. 636-644 (Year: 2014).*

Nardelli et al., "Optimizing parameters of an open-source airway segmentation algorithm using different CT images," 2015, BioMed. Eng. OnLine, vol. 14, pp. 62 (Year: 2015).*

Steinfort et al. "Multinnodality guidance for accurate bronchoscopic insertion of fiducial markers", 2015, J Thorac Oncol. vol. 10, pp. 324-330 (Year: 2015).*

Canadian Office Action dated Oct. 18, 2017 in corresponding Canadian Patent Application No. 2,939,099, 3 pages.

European Search Report in corresponding European Application No. 16189890, dated Feb. 9, 2017, 9 pages.

Australian Examination Report No. 1 issued in corresponding Appl. No. AU 2018204573 dated Feb. 19, 2019 (4 pages).

Nolification of the First Office Action issued by the State Intellectual Property Office of the People's Republic of China dated Dec. 29, 2018 in corresponding Chinese Patent Application No. 201610845333.3, with English translation.

* cited by examiner

MARKER PLACEMENT

CROSS REFERENCE TO RELATED APPLICATIONS

The present application claims priority to earlier filed U.S. Provisional Patent Application No. 62/232,170 entitled "MARKER PLACEMENT" filed Sep. 24, 2015, the entire contents of which are incorporated herein by reference.

BACKGROUND

Technical Field

The present disclosure relates to the field of placing markers in a body region for therapeutic purposes and to Electromagnetic Navigation (EMN) assisted marker placement, in particular.

Description of Related Art

A common device for inspecting and navigating the airway of a patient is a bronchoscope. Typically, the bronchoscope is inserted into a patient's airways through the patient's nose or mouth and can extend into the lungs of the patient. A typical bronchoscope includes an elongated flexible tube having an illumination assembly for illuminating the region distal to the bronchoscope's tip, an imaging assembly for providing a video image from the bronchoscope's tip, and a working channel through which instruments, e.g., diagnostic instruments such as biopsy tools and therapeutic instruments may be inserted.

In navigating to a target, bronchoscopes, however, are limited in how far they may be advanced through the airways due to their size. Where the bronchoscope is too large to reach a target location deep in the lungs a clinician may utilize certain real-time imaging modalities such as fluoroscopy. Fluoroscopic images, while useful present certain drawbacks for navigation as it is often difficult to distinguish luminal passageways from solid tissue. Moreover, the images generated by the fluoroscope are two-dimensional whereas navigating the airways of a patient requires the ability to maneuver in three dimensions.

To address these aforementioned issues, systems and methods have been developed that enable the development of three-dimensional models of the airways or other luminal networks, typically from a series of computed tomography (CT) images. One such system has been developed as part of the ILOGIC® ELECTROMAGNETIC NAVIGATION BRONCHOSCOPY® (ENB™), system currently sold by Covidien LP. The details of such a system are described in the commonly assigned U.S. Pat. No. 7,233,820 filed on Mar. 29, 2004 to Gilboa and entitled ENDOSCOPE STRUCTURES AND TECHNIQUES FOR NAVIGATING TO A TARGET IN BRANCHED STRUCTURE, the contents of which are incorporated herein by reference.

Actual and potential uses for Electromagnetic Navigation Bronchoscopy (ENB) may include biopsy of peripheral lung lesions, pleural dye marking of nodules for surgical wedge resection, placement of fiducial markers for stereotactic radiotherapy, and therapeutic insertion of brachytherapy catheters into malignant tissue.

In particular, the benefits of using ENB to place fiducial markers for stereotactic radiotherapy or radiosurgery is becoming increasingly recognized. An example for a radio-surgery system is the Cyberknife® system (manufactured by Accuray Inc., Sunnyvale, Calif.). Treatment for inoperable lung cancer using stereotactic radio surgery rather than external beam radiotherapy allows delivery of precisely targeted radiation to the tumor while minimizing dosage to adjacent tissue. Nevertheless, fiducial markers first have to be accurately placed, either transthoracically, intravascularly, or bronchoscopically, to enable tracking of the tumor. Despite the latter being the safest method, bronchoscopically placed markers are essentially placed "blindly" because the tumor cannot be directly visualized. Using the navigational ability of ENB may improve placement accuracy.

While the system as described in U.S. Pat. No. 7,233,820 is quite capable, there is always a need for development of improvements and additions to such systems.

SUMMARY

There is provided in accordance with the present disclosure, a method for placing a set of one or more markers in a luminal network in a patient's body, the method comprising using at least one hardware processor for: receiving image data of the anatomy of a luminal network of a patient and a location of at least one target in said luminal network anatomy; obtaining a rule set defining one or more rules for placing said set of one or more markers in said luminal network anatomy and with respect to said at least one target; during a survey performed by a user via a navigation system in a portion of the luminal network surrounding said at least one target, acquiring, via said navigation system, sample-locations in the surveyed portion of the luminal network; and identifying a set of one or more marker locations for placing said set of one or more markers from said acquired sample-locations, which complies with said rule set.

There is further provided in accordance with the present disclosure, a system for navigating to a target through a luminal network in a patient's body, the system comprising: a navigation system configured to navigate through said luminal network; and a workstation in operative communication with said navigation system, the workstation comprising: (i) a storage device having stored thereon instructions for: receiving image data of the anatomy of the luminal network and a location of at least one target in said thoracic anatomy, obtaining a rule set defining one or more rules for placing a set of one or more markers in said luminal network anatomy and with respect to said at least one target, during a survey performed by a user in a portion of said luminal network surrounding said target while using said navigation system, acquiring, via said navigation system, sample-locations in the surveyed portion of the luminal network, and identifying a set of one or more marker locations for placing said set of one or more markers from said acquired sample-locations, which comply with said rule set, and (ii) at least one hardware processor configured to execute said instructions.

There is further provided in accordance with the present disclosure, a computer program product comprising a non-transitory computer-readable storage medium having program code embodied therewith, the program code executable by at least one hardware processor to: receive image data of a body region of a patient comprising a luminal network and at least one target location in said body region; obtain a rule set defining one or more rules for placing a set of one or more markers in said body region and with respect to said at least one target; during a survey performed by a user via a navigation system in the luminal network surrounding said target, acquire, via said navigation system, sample-locations in the surveyed lumens of said luminal network; and identify a set of one or more marker locations for placing said set of said one or more markers from said acquired sample-locations, which comply with said rule set.

In another aspect of the present disclosure, said one or more marker locations are one or more marker regions, and wherein each of said one or more marker regions comprises a plurality of locations which comply with said rule set.

In another aspect of the present disclosure, said one or more marker regions are spheres having a radius size selected from the group consisting of: up to 7 mm and 7 mm±1 mm.

In another aspect of the present disclosure, said method further comprises using said at least one hardware processor for generating a display comprising the path of said survey superimposed on said image data of said luminal network anatomy, and wherein said path is comprised of said acquired sample-locations.

In another aspect of the present disclosure, said method further comprises using said at least one hardware processor for: generating a display comprising indications of said one or more marker locations superimposed on said image data of said luminal network anatomy; and instructing said user in placing said one or more markers in said one or more marker locations via said display.

In another aspect of the present disclosure, said user is instructed to place at least one of said one or more markers in tissue external to said luminal network, in the vicinity of said one or more marker locations.

In another aspect of the present disclosure, said user fails to place a marker of said one or more markers in a marker location of said set of one or more marker locations, the method further comprising using said at least one hardware processor for: acquiring a current location of said user in said luminal network anatomy; if said current location complies with said rule set, determining said current location as the marker location for said marker; and identifying marker locations from said acquired sample-locations for placing non placed markers of said set of one or more markers, wherein said identifying of said marker locations is performed with respect to said current location and in accordance with said rule set.

In another aspect of the present disclosure, said rule set comprises rules selected from the group consisting of: distance of each of said one or more markers from said target, distance between each two of said one or more markers, an angle separation between two of said one or more markers and a diameter of a lumen of said luminal network.

In another aspect of the present disclosure, said method further comprises using said at least one hardware processor for: obtaining data comprising a location of a previous marker which was previously placed in said patient's luminal network; and if said previous marker location complies with said rule set, determining said previous marker as a marker of said set of one or more markers which is placed in a marker location, wherein identifying of the remainder of said one or more marker locations is performed with respect to said previous marker location and said rule set.

In another aspect of the present disclosure, said acquiring of said sample-locations and said identifying of said set of one or more marker locations comprise repeatedly acquiring a plurality of sample locations until at least one set of one or more marker locations complying with said rule set is identified in the acquired sample locations.

In another aspect of the present disclosure, said luminal network is the airways in said patient's thorax.

In another aspect of the present disclosure, said luminal network is said patient's bronchial tree and wherein: said navigation system comprises: a bronchoscope configured for insertion into a patient's bronchial tree, the bronchoscope defining a working channel; and a locatable guide insertable into the working channel of the bronchoscope and configured to navigate through the patient's bronchial tree, the locatable guide comprising a location sensor, said workstation is in operative communication with the locatable guide and the bronchoscope, said survey is performed by said user in the airways of the patient's bronchial tree surrounding said target while using said locatable guide, and said acquiring of said sample-locations is performed via said location sensor.

In another aspect of the present disclosure, said system further comprises a display, wherein said storage device has further instructions stores thereon for: displaying on said display indications of said one or more marker locations superimposed on said image data of said thoracic anatomy; and instructing said user in placing said one or more markers in said one or more marker locations via said display.

In another aspect of the present disclosure, said storage device has further instructions stores thereon for displaying on said display the path of said survey superimposed on said image data of said thoracic anatomy, and wherein said path is comprised of said acquired sample-locations.

In another aspect of the present disclosure, said user fails to place a marker of said set of said one or more markers in a marker location of said set of said one or more marker locations, and wherein said storage device has stored thereon further instructions for: acquiring a current location of said marker in said thoracic anatomy; and if said current location complies with said rule set, determining said current location as the marker location for said marker; and identifying of marker locations from said acquired sample-locations for placing non placed markers of said set of one or more markers, wherein said identifying of said marker locations is performed with respect to said current location and in accordance with said rule set.

In another aspect of the present disclosure, said storage device has further instructions stores thereon for: obtaining data comprising a location of a previous marker which was previously placed in said patient's thorax; and if said previous marker location complies with said rule set, determining said previous marker as a marker of said set of said one or more markers which is placed in a marker location, wherein identifying of the remainder of said one or more marker locations is performed with respect to said previous marker location and said rule set.

Any of the above aspects and embodiments of the present disclosure may be combined without departing from the scope of the present disclosure.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. The figures are listed below.

DETAILED DESCRIPTION

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing," "computing," "calculating," "determining," "inferring", "deducing", "establishing", "analyzing", "checking", or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the embodiments of methods described herein are not constrained to a particular order or sequence of steps, operations or procedures. Additionally, some of the described method embodiments or elements thereof can occur or be performed at the same point in time.

Disclosed herein is a method, a system and a computer program product for placing a set of one or more markers in a region of a body, which includes a luminal network (e.g., the bronchial tree or the cardiovascular system). The disclosed marker placement may guide and/or aid a user, typically a physician, in placing a set of markers in the body region (e.g., the thorax) through its luminal network (e.g., the bronchial tree) via a navigation system and according to a predefined rule set. Such a rule set may be derived, for example, from anatomical constraints, the purpose of the marker placement and/or the requirements of a therapeutic device or tool to be used with the markers. Such a rule set may include rules relating to a deployment of the markers in a specific geometrical structure, minimal and/or maximal distance and/or angle between the deployed markers and/or minimal distance between the deployed markers and blood vessels or other body organs or regions of interest and the like.

For example, the Cyberknife® system may be used to treat tumors in the lungs by delivering beams of high dose radiation to the tumors. This treatment may require a preliminary procedure of placement of fiducial markers in order to identify the exact location of the tumor (i.e., a target) during the treatment. The placement of the fiducial markers should be according to the system predefined requirements. Such exemplary requirements include: placing three fiducial markers more than 20 millimeters (mm) apart and with a separation of an angle of more than 15° and at a distance between 25 to 55 mm from the center of the target.

Without any guidance, i.e., by using visual estimation only, placement of the fidcucial markers according to such requirements may be a difficult and a complex task for the physician and may result in an inaccurate placement. Inaccurate placement may reduce the efficiency of the treatment and even cause unnecessary damage to the patient. Thus, providing the physician with a suggestion for a layout of the markers in the desired body region, which complies with the requirements, may be of great benefit.

However, due to the branched and tapering structure of the bronchial tree, a physician may not necessarily be able to navigate to such one or more suggested marker locations. Furthermore, 3D models of bronchial trees may typically model only a portion of the bronchial tree (for example, due to blurry images or an obstruction) and may lack at least its most peripheral parts. Typically, such suggestions for marker locations are based on locations identified via such models. Thus, such suggestions may not consider locations which are not included in the 3D model of the bronchial tree, and therefore may miss locations for placing markers (or a layout of such) which may be better or more suitable to the task in hand.

The disclosed marker placement provides a user (e.g., a physician or a care giver) with a suggestion for a layout of a predefined set of markers in a desired body region which complies with a predefined rule set. The suggested layout is based on locations sampled during a dedicated survey conducted by the user in the vicinity of the target and in real time (i.e., proximate to the time of the actual placement of the makers). Thus, the suggested layout necessarily includes locations which have recently been visited by the user and therefore have high probability of being reached again. Moreover, the sampled locations may extend beyond the 3D model and since the locations are sampled in real time, they may further comply with the current location, position and/or state of the patient's airways.

In addition, the disclosed marker placement provides real-time guidance to a user during the deployment of the markers, which may provide great user flexibility in placing of the markers. In case the user fails to deploy a marker in a suggested location, e.g., since the user can not currently reach the location, the disclosed marker placement may provide a new suggestion which incorporates the current location of the user (i.e., the current location of a locatable guide operated by the user), whether this current location was acquired previously by the system during the user's survey, or not.

According to the disclosed marker placement, a user may be instructed to use a navigation system, e.g., an ENB system, to navigate to a target in a patient's thorax. Next, the user may be instructed to perform a survey in a portion of the luminal network surrounding the target, i.e., the airways surrounding the target. A suggestion or a recommendation for placing a predefined number of markers, i.e., a set of markers, proximal to the target may be then introduced to the user (e.g., on a display via a user interface) based on the survey. The user may confirm the suggestion. The user may then navigate to a marker location via the ENB system. Once the user arrives at the marker location, he may deploy a marker in this location. A display may provide real-time feedback to the user including the progress and/or path of navigation, success or failure of marker deployment in a marker location and if other locations, indicated by the user, may be used as alternative marker locations.

The term "marker", as referred to herein, may relate to any therapeutic or therapeutically related element that may be deployed, placed or released in a patient's body, including a fiducial marker and a therapeutic agent (e.g., a medicament).

The term "set" and "layout", as referred to herein with respect to markers or locations may relate to one or more markers or locations.

The term "target", as referred to herein, may relate to any element or a region of interest in a patient's body, and may include a clinical finding such as a tumor.

The terms "deployed", "placed", or "positioned" and their derivations may be used interchangeably with respect to markers throughout the application.

An Electro-Magnetic Navigation (EMN) procedure generally involves at least two phases: (1) planning a pathway to a target located within, or adjacent to, the patient's airways; and (2) navigating a locatable guide to the target along the planned pathway. These phases are generally referred to as (1) "planning" and (2) "navigation". The planning phase of an EMN procedure is more fully described in commonly-owned U.S. patent application Ser. Nos. 13/838,805; 13/838,997; and Ser. No. 13/839,224, all entitled "Pathway Planning System and Method", filed on Mar. 15, 2013, by Baker, the entire contents of which are hereby incorporated by reference.

Prior to the planning phase, the patient's lungs are imaged by, for example, a computed tomography (CT) scan, although additional applicable methods of imaging will be known to those skilled in the art. The image data assembled during the CT scan may then be stored in, for example, the Digital Imaging and Communications in Medicine (DICOM) format, although additional applicable formats will be known to those skilled in the art. The CT scan image data may then be loaded into a planning software application ("application") to be used during the planning phase of the ENB procedure.

Figure 1:
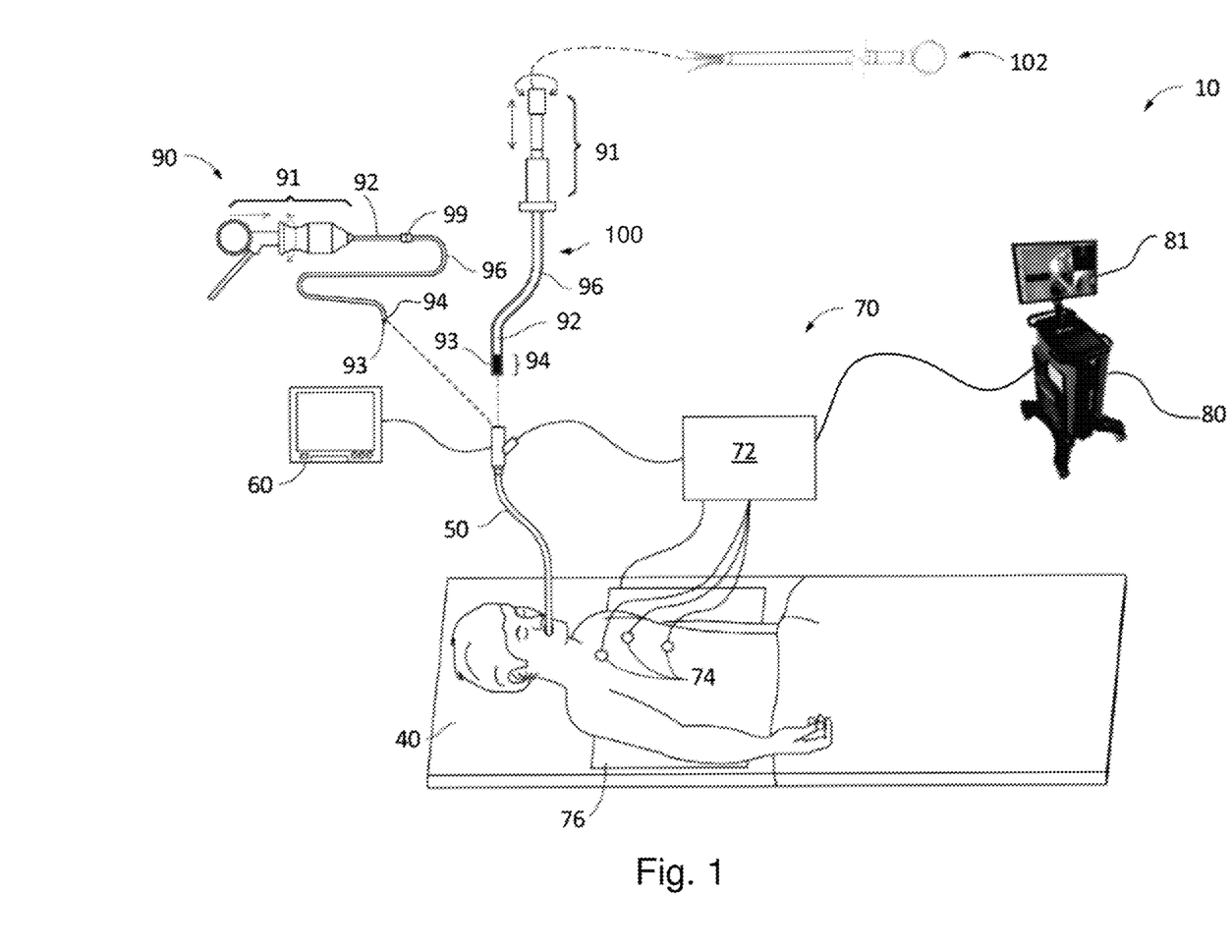
FIG. 1 is a perspective view of an exemplary electromagnetic navigation system in accordance with the present disclosure.

With reference to FIG. 1, an exemplary electromagnetic navigation (EMN) system 10 is provided in accordance with the present disclosure. One such ENM system is the ENB® system currently sold by Covidien LP. Among other tasks that may be performed using the EMN system 10 are planning a pathway to target tissue, navigating a positioning assembly to the target tissue, navigating a biopsy tool to the target tissue to obtain a tissue sample from the target tissue using the biopsy tool, and digitally marking the location where the tissue sample was obtained, and placing one or more markers at or around the target.

EMN system 10 may generally include an operating table 40 configured to support a patient; a bronchoscope 50 configured for insertion through the patient's mouth and/or nose into the patient's bronchial tree (i.e., airways), the bronchoscope defining a working channel; monitoring equipment 60 operatively coupled with bronchoscope 50 for displaying video images received from bronchoscope 50; a tracking system 70, which may include a tracking module 72, a plurality of reference sensors 74 and an electromagnetic field generator 76; a workstation 80, which may include software and/or hardware used, e.g., to facilitate pathway planning, identification of target tissue, navigation to target tissue, and digitally marking the biopsy location.

FIG. 1 also depicts two types of catheter guide assemblies 90 and 100. Both catheter guide assemblies 90, 100 may be usable with EMN system 10 and may share a number of common components. Each catheter guide assembly 90, 100 may include a handle 91, which may be connected to an extended working channel (EWC) 96. EWC 96 may be sized for placement into the working channel of bronchoscope 50. In operation, a locatable guide (LG) 92, including a location sensor, such as an electromagnetic (EM) sensor 94, may be inserted into EWC 96 and locked into position such that sensor 94 extends a desired distance beyond the distal tip 93 of EWC 96. LG 92 may be configured to navigate through a patient's bronchial tree. The location of EM sensor 94, and thus the distal end of the EWC 96, within an electromagnetic field generated by electromagnetic field generator 76 may be derived by tracking module 72, and workstation 80. Catheter guide assemblies 90, 100 may have different operating mechanisms, but each may contain handle 91 that may be manipulated by rotation and compression to steer distal tip 93 of LG 92 through extended working channel 96. Catheter guide assemblies 90 are currently marketed and sold by Covidien LP under the name SUPERDIMENSION® Procedure Kits, similarly catheter guide assemblies 100 are currently sold by Covidien LP under the name EDGE™ Procedure Kits, both kits may include handle 91, extended working channel 96, and locatable guide 92. For a more detailed description of the catheter guide assemblies 90, 100 reference is made to commonly-owned U.S. patent application Ser. No. 13/836,203 filed on Mar. 15, 2013 by Ladtkow et al., the entire contents of which are hereby incorporated by reference.

As illustrated in FIG. 1, the patient is shown lying on operating table 40 with bronchoscope 50 inserted through the patient's mouth and into the patient's airways. Bronchoscope 50 may include a source of illumination and a video imaging system (not explicitly shown) and may be coupled with monitoring equipment 60, e.g., a video display, for displaying the video images received from the video imaging system of bronchoscope 50.

Catheter guide assemblies 90, 100 including LG 92 and EWC 96 may be configured for insertion through a working channel of bronchoscope 50 into the patient's airways (although the catheter guide assemblies 90, 100 may alternatively be used without bronchoscope 50). LG 92 and EWC 96 may be selectively lockable relative to one another via a locking mechanism 99. A six degrees-of-freedom electromagnetic tracking system 70, e.g., similar to those disclosed in U.S. Pat. No. 6,188,355 and published PCT Application Nos. WO 00/10456 and WO 01/67035, the entire contents of each of which is incorporated herein by reference, or any other suitable positioning measuring system, may be utilized for performing navigation, although other configurations are also contemplated. Tracking system 70 may be configured for use with catheter guide assemblies 90, 100 to track the position of EM sensor 94 as it moves in conjunction with EWC 96 through the airways of the patient, as detailed below.

As shown in FIG. 1, electromagnetic field generator 76 may be positioned beneath the patient. Electromagnetic field generator 76 and the plurality of reference sensors 74 may be interconnected with tracking module 72, which may derive the location of each reference sensor 74 in six degrees of freedom. One or more of reference sensors 74 may be attached to the chest of the patient. The six degrees of freedom coordinates of reference sensors 74 may be transmitted to workstation 80, which may include an application that may utilize sensors 74 to calculate a patient coordinate frame of reference.

Also shown in FIG. 1, there is a catheter biopsy tool 102 that may be insertable into the catheter guide assemblies 90, 100 following navigation to a target and removal of the LG 92. Biopsy tool 102 may be used to collect one or more tissue samples from the target tissue. As detailed below, biopsy tool 102 may be further configured for use in conjunction with tracking system 70 to facilitate navigation of biopsy tool 102 to the target tissue, tracking of a location of biopsy tool 102 as it is manipulated relative to the target tissue to obtain the tissue sample, and/or marking the location where the tissue sample was obtained. Catheter biopsy tool 102 is only an example for medical tools which may be used with the disclosed system. Tools such as a tool for placing or releasing a marker may be also used in a similar manner.

Although navigation is detailed above with respect to EM sensor 94 being included in LG 92, it is also envisioned that EM sensor 94 may be embedded or incorporated within biopsy tool 102 or any other tool, where biopsy tool 102 may alternatively be utilized for navigation without need of the LG or the necessary tool exchanges that use of the LG requires. A variety of useable biopsy tools are described in U.S. Provisional Patent Application Nos. 61/906,732 and 61/906,762 both entitled DEVICES, SYSTEMS, AND METHODS FOR NAVIGATING A BIOPSY TOOL TO A TARGET LOCATION AND OBTAINING A TISSUE SAMPLE USING THE SAME, filed Nov. 20, 2013 and U.S. Provisional Patent Application No. 61/955,407 having the same title and filed Mar. 14, 2014, the entire contents of each of which are incorporated herein by reference and useable with the EMN system 10 as described herein.

During procedure planning, workstation 80 may utilize computed tomographic (CT) image data for generating and viewing a three-dimensional model ("3D model") of the patient's airways, enable the identification of target tissue on the 3D model (automatically, semi-automatically or manually), and allow for the selection of a pathway through the patient's airways to the target tissue. More specifically, the CT scans may be processed and assembled into a 3D volume, which may be then utilized to generate the 3D model of the patient's airways. The 3D model may be presented on a display monitor 81 associated with workstation 80, or in any other suitable fashion. Using workstation 80, various slices of the 3D volume and views of the 3D model may be presented and/or may be manipulated by a clinician to facilitate identification of a target and selection of a suitable pathway through the patient's airways to access the target. The 3D model may also show indications such as marks of the locations where previous biopsies were performed or previously placed markers including the dates, times, and other identifying information regarding these biopsy locations or markers. These indications may also be selected as the target to which a pathway may be planned. Once selected, the pathway is saved for use during the navigation procedure. An example of a suitable pathway planning system and method is described in U.S. patent application Ser. Nos. 13/838,805; 13/838,997; and Ser. No. 13/839,224, all entitled "PATHWAY PLANNING SYSTEM AND METHOD", filed on Mar. 15, 2014, the entire contents of each of which are incorporated herein by reference.

Figure 2:
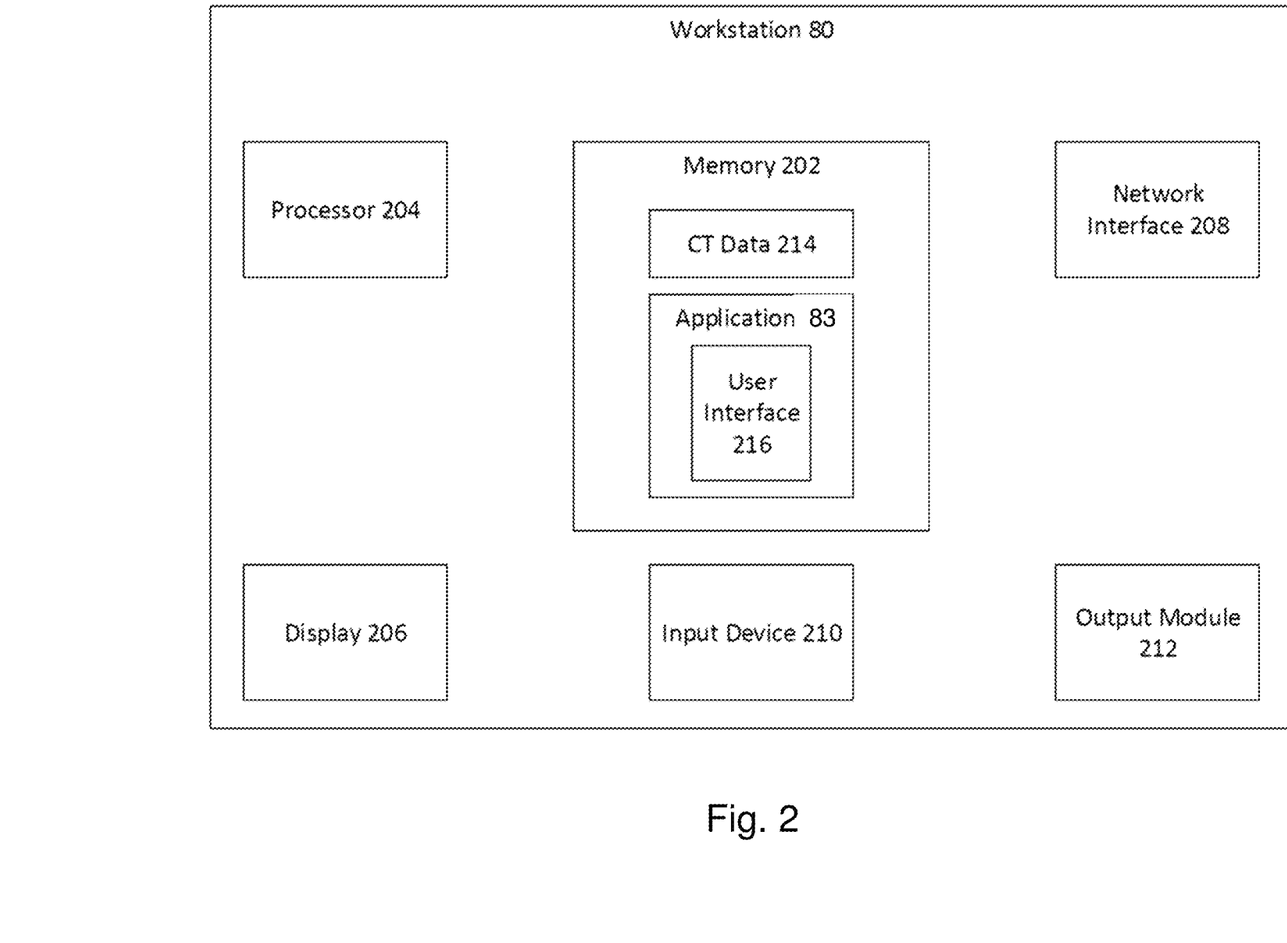
FIG. 2 is a schematic diagram of a workstation configured for use with the system of FIG. 1.

Turning now to FIG. 2, there is shown a system diagram of workstation 80. Workstation 80 may include memory 202, processor 204, display 206, network interface 208, input device 210, and/or output module 212. Memory 202 may store an application 83.

Prior to the start of navigation, the clinician loads a navigation plan including the 3D model of the lungs of the patient and the planned pathways to identified targets into navigation application 83 from memory 202, via network interface 208, or a USB drive. An example of the navigation application can be found in commonly assigned U.S. Provisional Patent Application No. 62/020,240 filed Jul. 2, 2014 and entitled SYSTEM AND METHOD FOR NAVIGATING WITHIN THE LUNG, the entire contents of which are incorporated herein by reference.

During navigation, EM sensor 94, in conjunction with tracking system 70, enables tracking of EM sensor 94 and/or biopsy tool 102 as EM sensor 94 or biopsy tool 102 is advanced through the patient's airways.

Memory 202 may include any non-transitory computer-readable storage media for storing data and/or software that is executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable media contained herein refers to a solid-state storage, it should be appreciated by those skilled in the art that computer-readable storage media can be any available media that can be accessed by the processor 204. That is, computer readable storage media may include non-transitory, volatile and non-volatile, removable and non-removable media implemented in any method or technology for storage of information such as computer-readable instructions, data structures, program modules or other data. For example, computer-readable storage media may include random access memory (RAM), read-only memory (ROM), erasable programmable read-only memory (EPROM), electrically erasable programmable read-only memory (EEPROM), flash memory or other solid state memory technology, compact disc ROM (CD-ROM), digital versatile disc (DVD), Blu-Ray or other optical storage, magnetic cassettes, magnetic tape, magnetic disk storage or other magnetic storage devices, or any other medium which may be used to store the desired information and which may be accessed by workstation 80.

Memory 202 may store an application 83 and/or CT data 214. Application 83 may, when executed by processor 204, cause display 206 to present user interface 216. Network interface 208 may be configured to connect to a network such as a local area network (LAN) consisting of a wired network and/or a wireless network, a wide area network (WAN), a wireless mobile network, a Bluetooth network, and/or the internet. Input device 210 may be any device by means of which a user may interact with workstation 80, such as, for example, a mouse, keyboard, foot pedal, touch screen, and/or voice interface. Output module 212 may include any connectivity port or bus, such as, for example, parallel ports, serial ports, universal serial busses (USB), or any other similar connectivity port known to those skilled in the art.

Memory 202 may include any non-transitory computer-readable storage medium including data, software and/or program code embodied therewith that are executable by processor 204 and which controls the operation of workstation 80. In an embodiment, memory 202 may include one or more solid-state storage devices such as flash memory chips. Alternatively or in addition to the one or more solid-state storage devices, memory 202 may include one or more mass storage devices connected to the processor 204 through a mass storage controller (not shown) and a communications bus (not shown). Although the description of computer-readable medium contained herein refers to a solid-state storage, it should be appreciated by those skilled in the art that computer-readable storage medium can be any available medium that can be accessed by the processor 204. That is, computer readable storage medium may include non-transitory, volatile and non-volatile, removable and non-removable media implemented in any method or technology for storage of information such as computer-readable instructions, data structures, program modules or other data. For example, computer-readable storage medium may include RAM, ROM, EPROM, EEPROM, flash memory or other solid state memory technology, CD-ROM, DVD, Blu-Ray or other optical storage, magnetic cassettes, magnetic tape, magnetic disk storage or other magnetic storage devices, or any other medium which can be used to store the desired information and which can be accessed by workstation 80.

EMN system 10 may be operated in accordance with the method of FIG. 3 and as described herein below.

Figure 3:
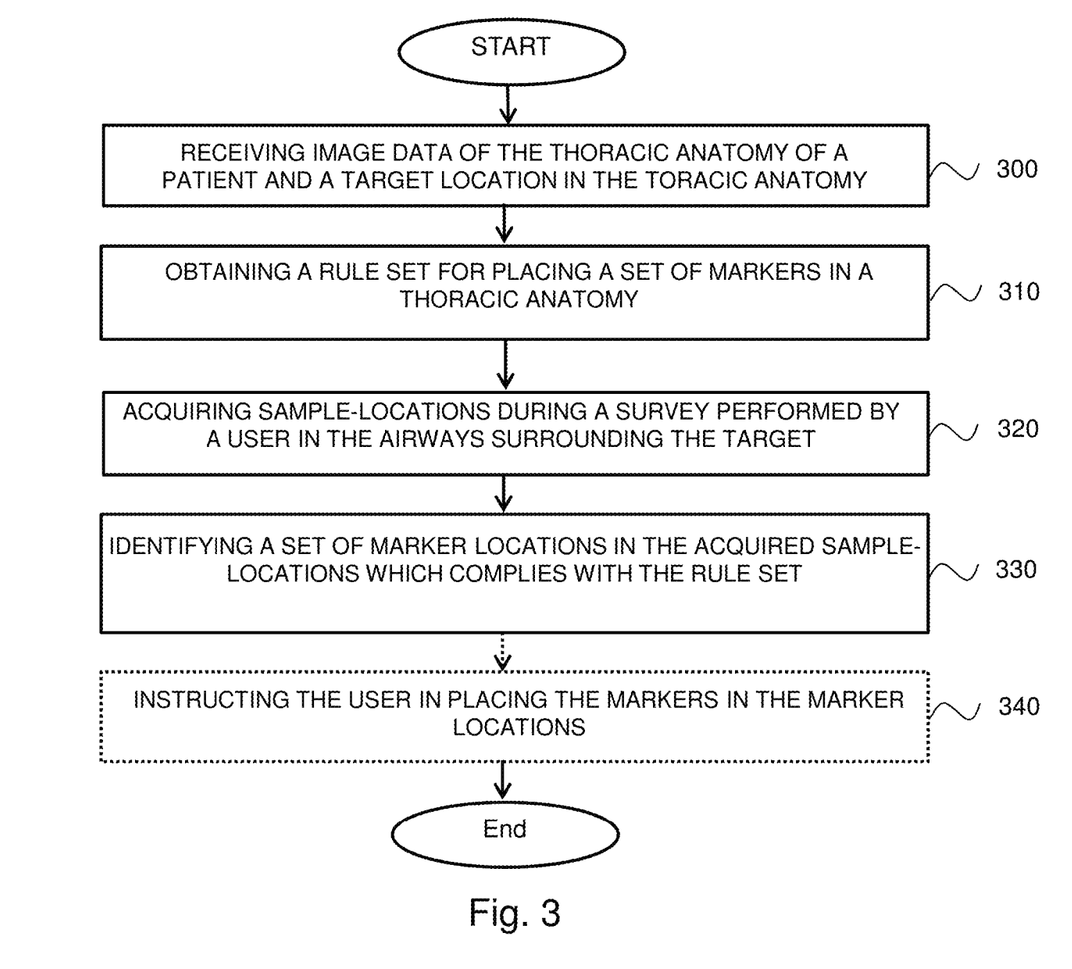
FIG. 3 is a flowchart illustrating an exemplary method for placing one or more markers in a patient's thorax in accordance with the present disclosure.

Referring now to FIG. 3, there is shown a flowchart of an exemplary method for placing a set of one or more markers (or simply 'the set of markers' or 'the markers') in a patient's thorax in accordance with the present disclosure. For example, the markers may be fiducial markers for facilitating irradiation of a tumor by the Cyberknife® system. With reference to FIG. 2, user interface 216 may further include a feature of marker placement for instructing the user to provide required input and perform a survey, provide the user with a suggested set of marker locations for placing the set of markers and/or instruct the user in deploying the markers in accordance with the obtained rule set and with such a suggestion in particular.

In a step 300, image data of the thoracic anatomy of a patient may be received. In addition, at least one target location in the thoracic anatomy of the patient, such as the location of a tumor, may be also received. The image data may be, for example, a CT scan image data previously acquired. The image data may demonstrate the target. Accordingly, the location of the target may be obtained from the image data. Alternatively, and with reference to FIG. 2, the target location may be received by a user indicating the target via input device 210 on display 206, while it displays the received image data. Multiple target locations may be received, while one or more of the markers may be placed for each of the targets in a separate manner. Alternatively, the multiple targets or a portion of the targets may be joined to one single target.

The image data may be automatically registered with the thoracic anatomy of the patient. Details of this registration are set forth in Provisional Application 62/020,220 filed on Jul. 2, 2014 the contents of which are incorporated herein by reference. Alternative registration techniques including manual registration are possible and described in detail in U.S. Pat. No. 7,233,820 entitled "Endoscope structures and techniques for navigating to a target in branched structure" the entire contents of which are incorporated herein by reference.

In a step 310, a rule set, defining one or more rules for placing the set of markers in the patient's thoracic anatomy may be obtained. The placement of the markers may be defined with respect to the target (e.g., the nature of the target and/or its location). The rule set may be received by a user input, e.g., via input device 210. According to some aspects of the disclosed marker placement, the rule set may be a template to be adapted according to the user's input. Thus, user interface 216 may present the user with a series of questions designed to facilitate the generation of a specific rule set based on the template. According to some other aspects, the rule set is obtained by predefining one or more rule sets. A predefined rule set may comply, for example, with the requirements of a certain procedure, anatomy and/or system or tools to be used, such as the requirements of the Cyberknife® system, as describe herein above. The user may select, via user interface 216 and display 206, such predefined rule sets. According to some further aspects of the disclosed marker placement, a rule set may be obtained by combining predefined requirements with user input. Such user input may relate, for example, to the number of markers to be placed according to predefined requirements. A rule set may include rules such as a minimal and/or maximal distance of each marker from the target, a minimal and/or maximal distance between each two markers, a minimal and/or maximal angle separation between the markers, a minimal diameter of airways (or a minimal diameter of the lumens in the luminal network, in case other luminal networks are concerned) and a minimal distance between a marker and a body organ such as blood vessels.

In a step 320, sample-locations may be acquired during a survey performed by a user in the airways surrounding the target via a navigation system. The sample-locations may be acquired from the surveyed airways and via the navigation system. The navigation system may be the ENB® system currently sold by Covidien LP. The sample-locations may be acquired in a continuous or intermitted manner, e.g., per a predefined time interval.

According to some aspects of the disclosed marker placement, one or more of the rules of the rule set may be already applied at this stage, i.e., while acquiring sample-locations. Such rules may be used as filters for acquiring sample-locations. For example, the rule set may include a rule relating to a maximal diameter of an airway, e.g., less than four mm. Accordingly, the acquisition of sample-locations may be performed only once the user reach airways having a diameter less than four mm. Basically, since the bronchial tree tapers as the user advances (i.e., via a guide inserted within), at some point, one may assume that the airways diameter is smaller than four mm. The diameter of the airways in the main or center portion of the patient's bronchial tree may be obtained from the 3D model of the patient's airways. In accordance with some aspects of the disclosed marker placement, once the user leaves the modeled portion of the bronchial tree and reaches its more peripheral and/or non-modeled portions, it may be assumed that the diameter of these non-modeled airways is smaller than four mm.

According to some aspects of the disclosed marker placement, one or more displays dedicated to the feature of marker placement may be generated. Referring back to FIG. 2, user interface 216 may include a button for activating the feature of marker placement. A dedicated screen may be then displayed on display 206. The screen may include views including navigation views, similar to the navigation phase according to the ILOGIC® ELECTROMAGNETIC NAVIGATION BRONCHOSCOPY® (ENB™) system currently sold by Covidien LP. For example, the default view configuration may include three views: a local view (i.e., a CT scan presented according to the plane defined by the locatable guide), a 3D map (i.e., the 3D model) and a bronchoscope view (i.e., the video images received from bronchoscope 50). However, other views may be displayed, for example, by using fluoroscopy. A target may be selected by the user. The target may be visualized and displayed on the different views as sphere in a specific color, e.g., a 10 mm green sphere. The user may be instructed to navigate to the target and initiate a survey in the airways surrounding the target.

In accordance with some aspects of the disclosed marker placement, an on screen indication of ongoing acquisition of sample-locations may be displayed. Furthermore, the display may include the path of the survey performed by the user superimposed on image data of the patient's thoracic anatomy. By 'superimposed on image data', it is meant superimposed on any view of the display which includes or is derived from the received image data. The displayed path may include at least a portion of the acquired sample-locations. The path may be displayed in one or more of the various views of the display.

Figure 4:
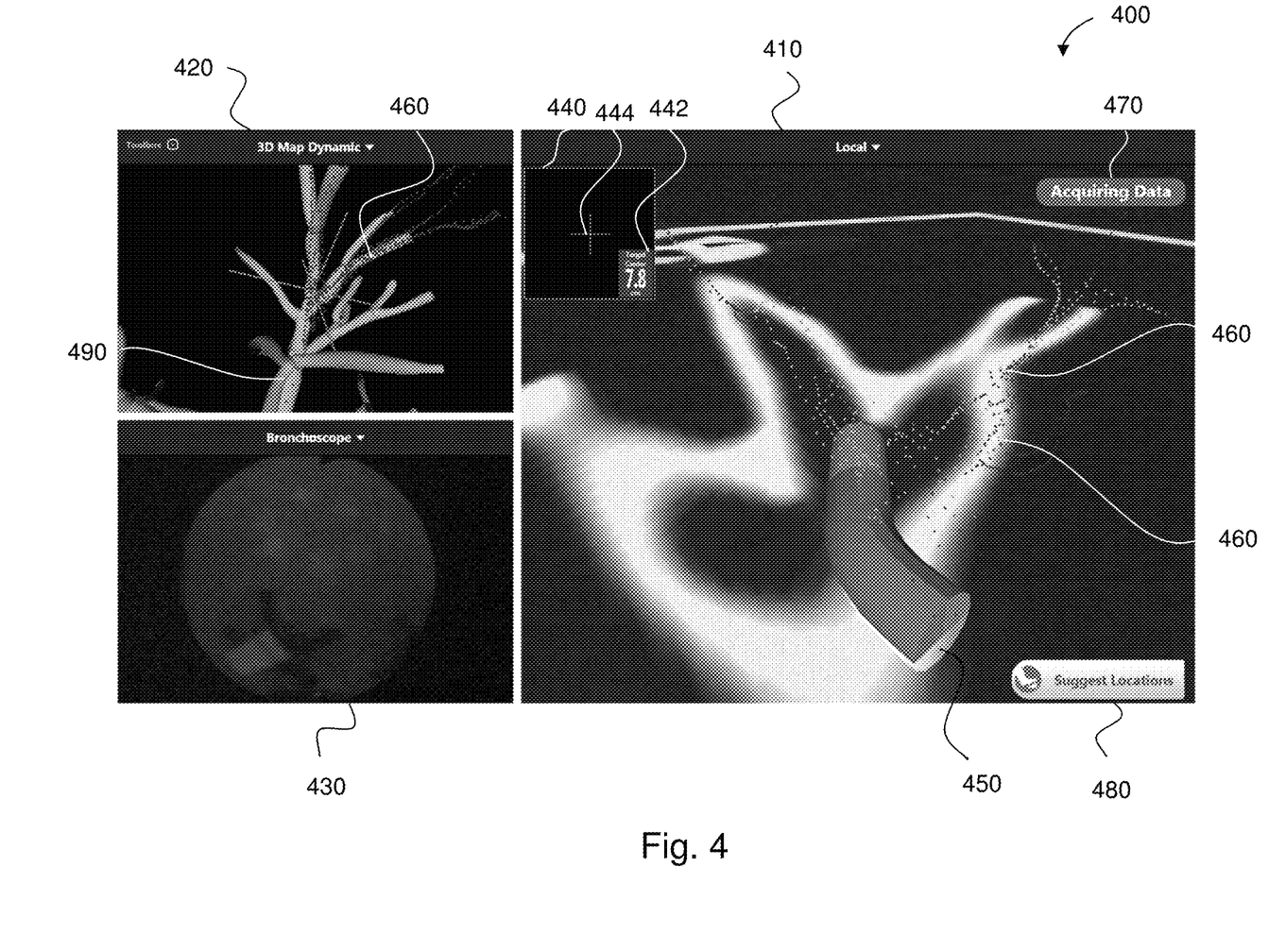
FIG. 4 shows a screen shot of an exemplary display, which is presented during a survey performed by a user.

Reference is now made to FIG. 4, which shows a screen shot of an exemplary display 400, which is presented during a survey performed by a user. Display 400 may include three views: a local view 410, a 3D map dynamic view 420 and a bronchoscope view 430. A Locatable-Guide (LG) 450 maneuvered by the user is shown in local view 410 superimposed on the image data of the patient's bronchial tree. Indications of the acquired sample-locations 460 are also superimposed on the image data in local view 410, forming a path of the user's survey. The acquired sample-locations are additionally shown in 3D map dynamic view 420. One may see that some of the acquired sample locations 460 extend beyond a 3D model of the patient's bronchial tree 490, as shown in view 420. In accordance with some aspects of the disclosed marker placement, indications of sample-locations 460 may be superimposed on any view (e.g., CT scans and/or 3D map views). An indication 470 stating: "Acquiring Data" informs the user that the acquisition of sample-locations is ongoing. A window 440 may indicate the current distance, denoted 442, between the distal tip of the locatable guide and a center of the target. A cross 444 indicates the center of the view.

The sample-locations may be acquired, displayed and used per target. According to some aspects of the disclosed marker placement, sample-locations acquired for a target may be used for another target. Optionally, the user may be provided with the option to restart the sample-locations acquisition. In such a case, all the already acquired sample-locations may be discarded.

The sample-locations acquisition may automatically end once enough sample-locations have been acquired. Enough sample-locations may be acquired once at least one set of marker locations is identified according to step 330 below. Optionally, the user may end the sample-locations acquisition, e.g., by clicking a button. With reference to FIG. 4, a button 480 titled "Suggest Locations" may be clicked in order to end the sample-locations acquisition and initiate the identification of marker locations according to step 330 below.

In a step 330, a set of one or more marker locations (or simply 'the set of marker locations' or 'marker locations') for placing the set of markers, which comply with said rule set, may be identified from said acquired sample-locations. The identification of a set of marker locations from the acquired sample-locations, which complies with the rule set, may be performed according to various techniques, as known in the art.

An exemplary technique for acquiring sample-locations and for identifying a set of marker locations is detailed herein below. The acquisition of the sample-locations may be performed repeatedly until at least one set of marker locations complying with the rule set is identified. Thus, a plurality of sample-locations may be acquired and then reviewed to identify a set of marker locations. If such a set is not identified, another plurality of sample-locations may be acquired and all of the sample-locations acquired until that point may be reviewed. The above process may be performed iteratively until a set of marker locations complying with the rule set is identified. The plurality of the sample-locations acquired each time may be, for example, a predefined fixed number, or a variable number of sample-locations, which may be acquired per a predefined time interval (e.g., three seconds). At this stage, no further sample-locations may be acquired. The identified set of marker locations may be then suggested to the user as will be described in more details herein below.

Optionally, once a set of marker locations is identified, all of the possible sets of marker locations complying with the rule set may be identified in all of the sample locations acquired until that point. One set of marker locations may be selected from all of the identified sets of marker locations. The selection may be based on one or more predefined criterions. A predefined criterion may be, for example, a set of marker locations having a center (i.e., the center of the locations layout) which is the closest to the target and/or marker locations having the widest angle separation etc.

If the identification of at least one set of marker locations fails, for example, following an identification process which was initiated too early by the user (e.g., by clicking button 480), a message may be displayed to indicate that more sample-locations need to be acquired. Optionally, a user may be allowed to continue the survey, although enough sample-locations were acquired, in order to acquire additional sample-locations.

According to some aspects of the disclosed marker placement, the marker locations may be marker regions. A marker region may include a plurality of adjacent locations which may comply with said rule set. Accordingly, such a marker location may be, for example, a sphere. Such marker regions may be defined, for example, such that all or most of the possible sets of locations in these regions (i.e., by selecting one location from each region) comply with the rule set (e.g., 95% to 100% of the locations). A marker region may allow greater flexibility for the user in placing the marker and thus simplify the task of marker placement, while the larger the region is, the greater the flexibility is. However, on the other hand, regions which are too large may make the task of identifying a set of marker locations (i.e., marker regions) more difficult and time consuming. The marker region shape and/or size may be defined based on the specific rule set.

Referring back to FIG. 2, once a set of marker locations is identified or selected, it may be automatically displayed to the user on display 206. A display which includes indications of the set of marker locations superimposed on the image data of the thoracic anatomy may be generated. The indications of the marker locations may be in a form of a sphere. For example, it was found that marker regions in the shape of spheres having a radius of 7 mm±1 mm may comply with the rule set defined by Cyberknife® system requirements, as disclosed herein above, while allowing fine flexibility with a reasonable region size. Marker regions in the shape of a sphere having a radius of up to 7 mm may also comply with the specific rule set of Cyberknife® system.

Figure 5:
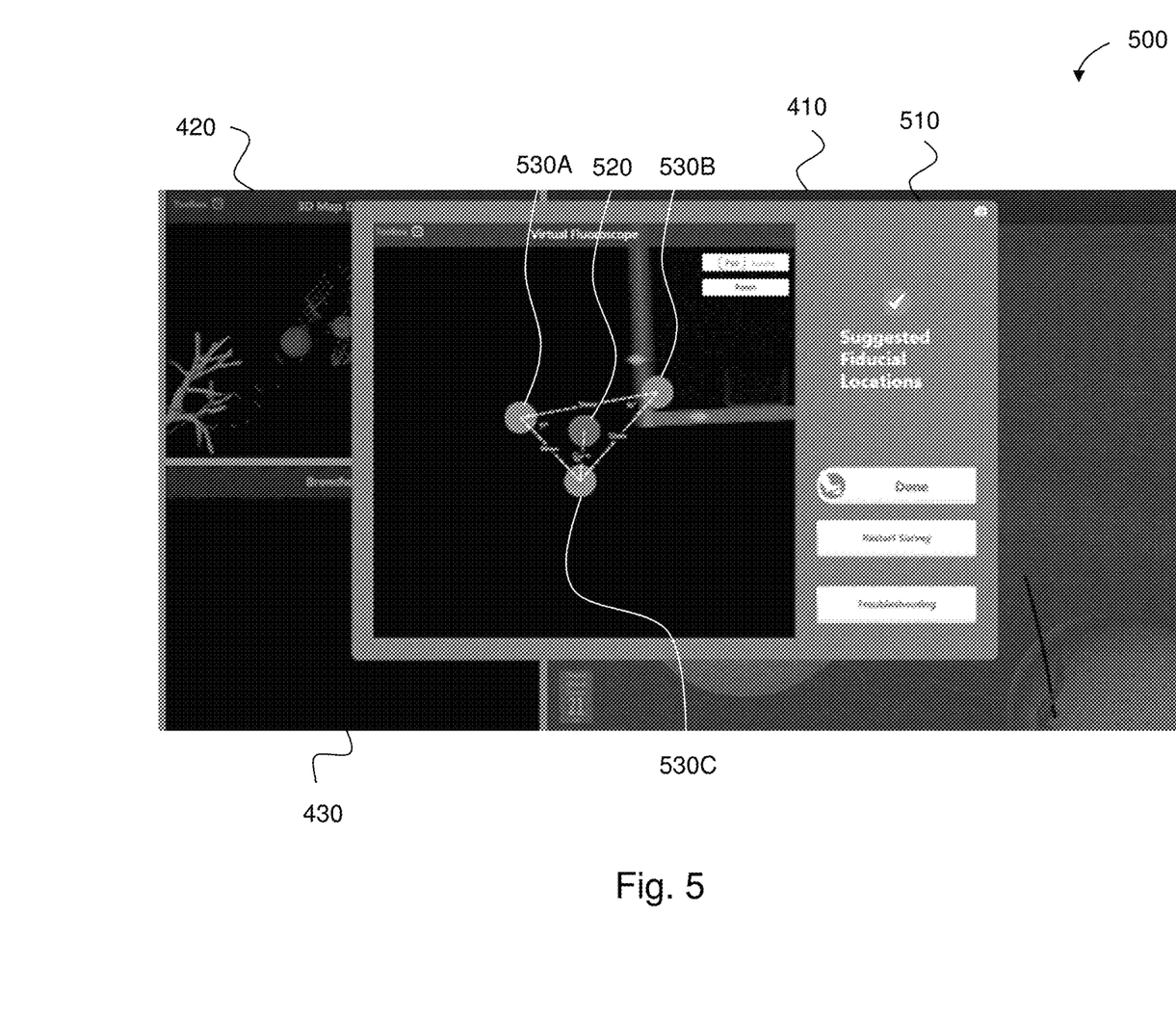
FIG. 5 shows a screen shot of an exemplary display, which presents the user with an exemplary suggested set of marker locations.

Reference is now made to FIG. 5, which shows a screen shot of an exemplary display 500 that presents the user with an exemplary suggested set of marker locations. Display 500 includes views 410, 420 and 430. Display 500 further includes a pop-up window 510. Pop-up window 510 may be initiated once a set of marker locations is identified or selected. Pop-up window 510 includes target 520, presented as a sphere in one color, and marker locations 530A, 530B and 530C, presented as spheres in a different color. The set of marker locations 530A, 530B and 530C complies with a rule set which was determined in accordance with the Cyberknife® system requirements. Marker locations 530A-

530C are placed around target 520 in a form of a triangle. Distances and angles between marker locations 530A-530C may be indicated as shown in pop-up window 510 (not denoted).

According to some aspects of the disclosed marker placement, previous locations of previously deployed markers may form a part of the currently suggested set of marker locations. Thus, deployment of one or more markers may be spared, mainly for the benefit of the patient, but also for the benefit of the user. Therefore, in a further step, data including a location of previous one or more markers, which were previously placed in the patient's thorax, may be obtained. Such data may be obtained, e.g., via a user input or extracted from the received image data.

If a previous marker location complies with the rule set, the marker may be determined as a marker of the set of markers to be deployed, which is already deployed. The identifying of the remainder of the marker locations may be then performed with respect to the previous marker location. In case the location of a previously deployed marker does not comply with the rule set, it may not be considered. In addition, an area surrounding this marker, having a predefined diameter, may be discarded and therefore may not be considered as a location for a marker in order to prevent misguidance or confusion.

According to some aspects of the disclosed marker placement, the user may be provided with the option to reject a suggested set of marker locations and/or with the option to restart a survey at any point. In such a case, the acquired sample-locations including the suggested marker-locations may be discarded. However, markers locations which are already deployed may not be discarded.

Referring back to FIG. 3 and according to an optional step 340, the user may be instructed in placing the markers in the marker locations via the display. As described herein above, the display may include various views of the patient's bronchial tree having indications of the target, the marker locations, the user's LG and/or the path of the user's survey superimposed thereon. The user may navigate through the bronchial tree and follow the survey path, via the LG, to the different marker locations.

Figure 6:
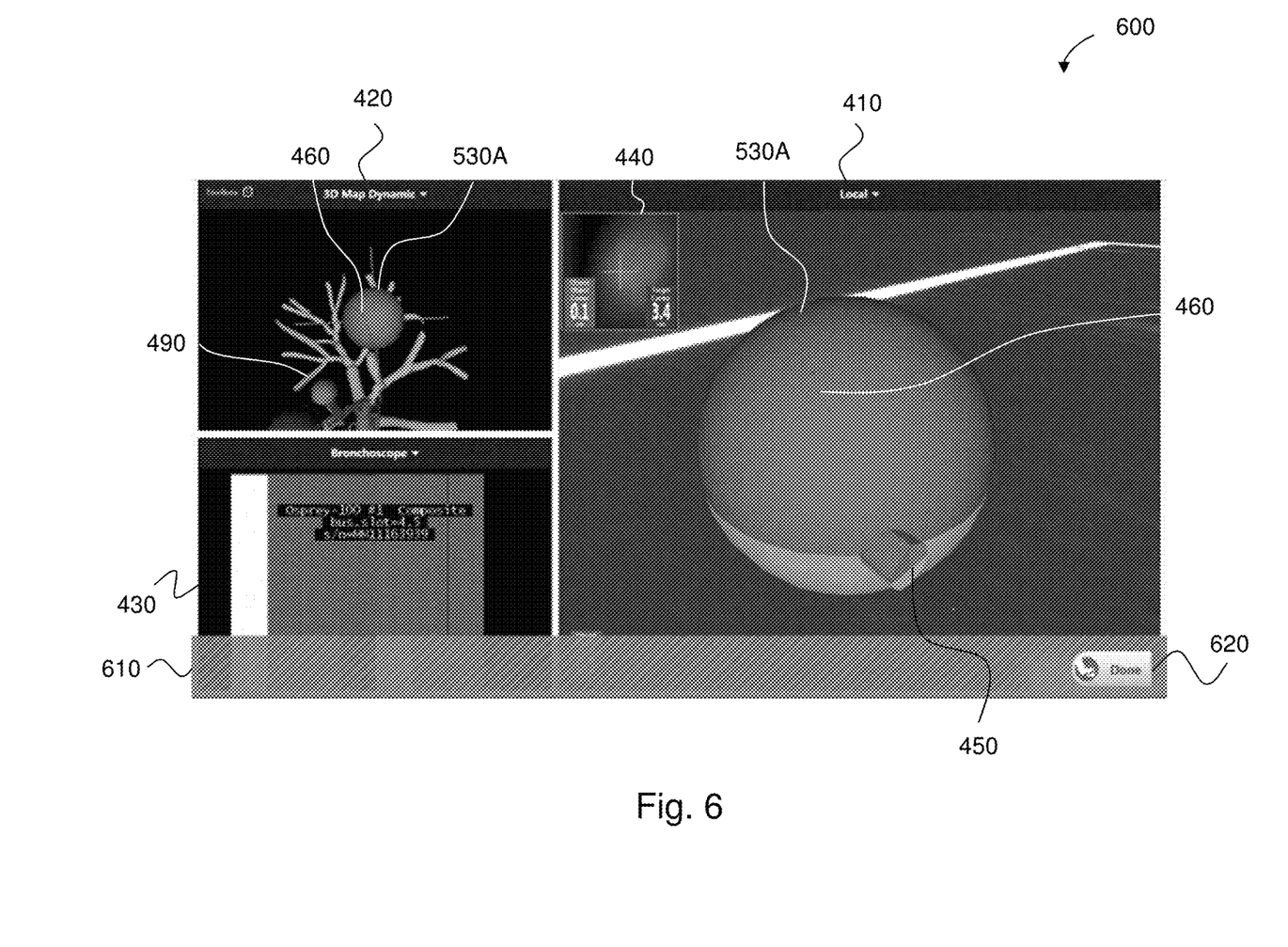
FIG. 6 shows a screen shot of an exemplary display, presenting a locatable guide in a marker location.

Once the user reaches a marker location, an indication may be displayed. For example, if the marker locations are marker regions, such as spheres, the color of such a sphere may change once the tip of the LG enters the sphere. Reference is now made to FIG. 6, which shows a screen shot of an exemplary display 600, presenting an LG in a marker location. Display 600 displays LG 450 in marker location 530A. Since marker location 530A is a sphere region including multiple locations, most of LG 450 is located within marker location 530A and therefore only the end of LG 450 is shown.

The user may then place or deploy a marker of the set of markers in the marker location. Indication of such deployment may be presented as well, e.g., by changing the color of the sphere to a different third color. When deploying a marker, the different views may be suspended. An indication for such a suspension may be presented, such as banner 610 of FIG. 6. Once the marker is deployed, the user may press a 'Done' button 620 to un-suspend the views. Once all of the markers are deployed in the suggested marker locations, the user may be presented with indication that the task is complete.

According to some aspects of the disclosed marker placement, the markers may be deployed in locations which are external to the luminal network, e.g., the airways. Accordingly, the user may be instructed to place one or more markers in tissue external to the luminal network, in the vicinity of the one or more marker locations. In such cases, the user may navigate to a marker location and then use an invasive tool, to reach the location for placing the marker, e.g., through an airway wall.

In some cases, a user may fail to place a marker in a marker location. Due to the branched and tapering structure of the bronchial tree, a change in the shape of the bronchial tree soft tissue (e.g., due to the user's actions) and/or breathing movements, a user may have difficulties in maneuvering and/or finding his way back to a location. The user may then request or indicate that he wishes to place the marker in a location different than any of the marker locations in the suggested set of marker locations. In such cases and in accordance with some aspects of the disclosed marker placement, the current location of the user may be acquired. It should be noted that such a location may be a sample location which was already acquired during the survey performed by the user or a new location, which was not acquired during the survey. By 'a current location of the user' it is meant a current location of the LG maneuvered by the user. If the current location complies with the rule set, then the current location may be determined as the marker location. Marker locations for placing the non-placed markers of the set of markers (i.e., the markers which were not placed yet) may be then identified from the acquired marker locations. The identification may be performed with respect to the current location and in accordance with the rule set. The already suggested marker locations may be reviewed first to check if they still comply with the rule set, when joined with the current location. Sample-locations which are adjacent to the already suggested marker locations may receive priority when identifying new locations for placing the remainder of the markers (i.e., the non-placed markers). Such course of action may make the procedure of identifying a new set of marker locations (or of updating the set of marker locations) more convenient for the user. If the current location does not comply with the rule set, a suitable message may be presented to the user. Other locations from the acquired sample-locations may be then reviewed in order to identify marker locations. If a new set of marker locations, which complies with the rule set, may not be identified, a new survey may be initiated.

In accordance with some aspects of the disclosed marker placement, a marker which is additional to the set of markers may be placed in the target. To allow such placement, the rule set may include dedicated rules such as a rule defining a minimal distance between a marker location and the target (e.g., a distance of 25 mm).

A computer program product for marker placement is further disclosed. The computer program product may include a non-transitory computer-readable storage medium having program code embodied therewith. The program code may be executable by at least one hardware processor, such as processor 204 of system 10 shown in FIG. 2. The program code may include application 81. The program code may include instructions for applying the method of FIG. 3 and as described herein above.

The method of FIG. 3, as described herein above, may be applied to other luminal networks with the required modifications, which will be obvious to one skilled in the art, and by using known navigation systems. The disclosed marker placement may be applied by using various navigation systems, including remote navigation such as remote magnetic navigation and with respect to various luminal networks. It should be noted that navigating a guide by a user according to the disclosed marker placement may be performed directly, i.e., by manually maneuvering the guide or indirectly or remotely, e.g., by using magnetic fields or robotic systems.

Further aspects which may relate to the disclosed marker placement and/or to ENB system 10 are described in co-pending and commonly-owned U.S. Provisional Patent Application Ser. No. 62/020,220 entitled "Real-Time Automatic Registration Feedback," filed on Jul. 2, 2014, by Brown et al.; U.S. Provisional Patent Application Ser. No. 62/020,177 entitled "Methods for Marking Biopsy Location," filed on Jul. 2, 2014, by Brown.; U.S. Provisional Patent Application Ser. No. 62/020,240 entitled "System and Method for Navigating Within the Lung," filed on Jul. 2, 2014, by Brown et al.; U.S. Provisional Patent Application Ser. No. 62/020,238 entitled "Intelligent Display," filed on Jul. 2, 2014, by Kehat et al.; U.S. Provisional Patent Application Ser. No. 62/020,242 entitled "Unified Coordinate System for Multiple CT Scans of Patient Lungs," filed on Jul. 2, 2014, by Greenburg.; U.S. Provisional Patent Application Ser. No. 62/020,245 entitled "Alignment CT," filed on Jul. 2, 2014, by Klein et al.; U.S. Provisional Patent Application Ser. No. 62/020,250 entitled "Algorithm for Fluoroscopic Pose Estimation," filed on Jul. 2, 2014, by Merlet; U.S. Provisional Patent Application Ser. No. 62/020,261 entitled "System and Method for Segmentation of Lung," filed on Jul. 2, 2014, by Markov et al.; U.S. Provisional Patent Application Ser. No. 62/020,253 entitled "Trachea Marking," filed on Jul. 2, 2014, by Lachmanovich et al.; and U.S. Provisional Patent Application Ser. No. 62/020,262 entitled "Dynamic 3D Lung Map View for Tool Navigation Inside the Lung," filed on Jul. 2, 2014, by Weingarten et al., the entire contents of all of which are hereby incorporated by reference.

Detailed embodiments of devices, systems incorporating such devices, and methods using the same have been described herein. However, these detailed embodiments are merely examples of the disclosure, which may be embodied in various forms. Therefore, specific structural and functional details disclosed herein are not to be interpreted as limiting, but merely as a basis for the claims and as a representative basis for allowing one skilled in the art to variously employ the present disclosure in virtually any appropriately detailed structure. The present disclosure is relevant to various types of imaging systems (e.g., fluoroscopic/radiographic imaging systems, etc.) and to various types of sensors. While the preceding embodiments were described in terms of bronchoscopy of a patient's airways, those skilled in the art will realize that the same or similar devices, systems, computer program products and methods may be used in or with respect to other lumen networks, such as, for example, the vascular, lymphatic, and/or gastrointestinal networks as well. Features of certain embodiments may be combined with features of other embodiments; thus certain embodiments may be combinations of features of other or multiple embodiments.

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

What is claimed is:

1. A computerized method for placing at least one marker in a luminal network in a patient's body, the method comprising:
   receiving image data of the luminal network of the patient and a location of at least one target in the luminal network;
   obtaining a rule set defining one or more rules for placing the at least one marker in the luminal network and with respect to the at least one target;
   receiving, at a tracking system, tracked locations of a sensor navigated within the luminal network in the vicinity of the at least one target based on the received location of the at least one target;
   using the tracked locations of the sensor in the vicinity of the at least one target to generate a survey of sample locations for placing the at least one marker within the patient's body;
   and
   identifying, from the sample locations, one or more marker locations for placing the at least one marker that comply with the rule set.

2. The method of claim 1, wherein the one or more marker locations are one or more marker regions, and each of the one or more marker regions comprises a plurality of locations which comply with the rule set.

3. The method of claim 2, wherein the one or more marker regions are spheres having a radius size that is greater than or equal to 6 mm and less than or equal to 8 mm.

4. The method of claim 1, further comprising generating a display including the survey of sample locations superimposed on the image data of the luminal network.

5. The method of claim 1, further comprising:
   generating a display including:
      indications of the one or more marker locations superimposed on the image data of the luminal network; and
      instructions to place the at least one marker in the one or more marker locations.

6. The method of claim 5, wherein the instructions are to place the at least one marker in tissue external to the luminal network, in the vicinity of the one or more marker locations.

7. The method of claim 1, wherein when the at least one marker is not placed in a marker location of the one or more marker locations, the method further comprises:
   acquiring a current location of the at least one marker in the luminal network;
   if the current location complies with the rule set, determining the current location as the marker location for the at least one marker; and
   identifying marker locations from the sample locations for placing a non-placed marker,
   wherein the marker locations are identified with respect to the current location and in accordance with the rule set.

8. The method of claim 1, wherein the at least one marker comprises at least two markers and the rule set comprises rules selected from the group consisting of:
   a distance of each of the at least two markers from the at least one target, a distance between each of the at least two markers, an angle separation between the at least two markers, and a diameter of a lumen of the luminal network.

9. The method of claim 1, further comprising:
   obtaining data including a previous marker location of a previous marker which was previously placed in the luminal network; and if the previous marker location complies with the rule set, determining the previous marker as being placed in one of the one or more marker locations,
wherein a remainder of the one or more marker locations is identified with respect to the previous marker location and the rule set.

10. The method of claim 1, wherein the luminal network is airways in the patient's thorax.

11. The method of claim 1 further comprising using the obtained rule set to filter sample locations from the survey during navigation of the sensor within the luminal network of the patient.

12. The method of claim 11, wherein using the obtained rule set to filter sample locations from the survey includes filtering sample locations based on a diameter of an airway of the luminal network in which the sensor is located as tracked by the tracking system.

13. The method of claim 1, wherein the at least one marker comprises at least two markers and the rule set comprises rules relating to a geometrical deployment of the at least two markers.

14. A non-transitory computer-readable storage medium having a program stored therein, which, when executed by at least one hardware processor, performs a method comprising:
receiving image data of a luminal network of a patient and a location of at least one target in the patient;
obtaining a rule set defining one or more rules for placing at least one marker in the patient and with respect to the at least one target;
receiving, at a tracking system, tracked locations of a sensor navigated within the luminal network in the vicinity of the at least one target based on the received location of the at least one target;
using the tracked locations of the sensor in the vicinity of the at least one target to generate a survey of sample locations for placing the at least one marker within the patient's body;
and
identifying, from the survey of sample locations, one or more marker locations for placing the at least one marker that comply with the rule set.

15. The non-transitory computer-readable storage medium of claim 14, wherein using the obtained rule set to filter sample locations from the survey includes filtering sample locations based on a diameter of an airway of the luminal network in which the sensor is located as tracked by the tracking system.

16. A method for placing a marker in a luminal network in a patient's body, the method comprising:
receiving image data of the luminal network of the patient and a location of a target in the luminal network;
receiving, at a tracking system, tracked locations of a sensor navigated within the luminal network in the proximity of the target based on the received location of the target;
using the tracked locations of the sensor to generate a survey of sample locations in proximity to the target for placing a marker within the patient's body during navigation of the sensor within the luminal network of the patient;
filtering sample locations from the survey during navigation of the sensor within the luminal network of the patient; and
identifying, from the filtered survey of sample locations, one or more marker locations for placing the marker.

17. The method of claim 16, wherein filtering sample locations from the survey includes filtering sample locations based on a diameter of an airway of the luminal network in which the sensor is located as tracked by the tracking system.

* * * * *